United States Patent [19]

Inacio et al.

[11] Patent Number: 4,925,377
[45] Date of Patent: May 15, 1990

[54] PUMP

[75] Inventors: Jorge Inacio, Solna; Erling Nilsson, Upplands Väsby, both of Sweden

[73] Assignee: Data Promeditech I.N.C. AB, Solna, Sweden

[21] Appl. No.: 199,260

[22] PCT Filed: Dec. 2, 1986

[86] PCT No.: PCT/SE86/00549

§ 371 Date: May 27, 1988

§ 102(e) Date: May 27, 1988

[87] PCT Pub. No.: WO87/03492

PCT Pub. Date: Jun. 18, 1987

[30] Foreign Application Priority Data

Dec. 5, 1985 [SE] Sweden .................. 8505753

[51] Int. Cl.⁵ ............................................ F04B 43/00
[52] U.S. Cl. ................................ 417/472; 417/478; 600/16; 92/117 R
[58] Field of Search ............ 417/472, 473, 478, 479, 417/480, 486, 487, 488, 542; 72/50, 98 D, 117 R, 36, 41; 600/16; 604/153; 623/3

[56] References Cited

U.S. PATENT DOCUMENTS

| | | | |
|---|---|---|---|
| 194,010 | 8/1877 | Stewart | 417/472 |
| 229,563 | 7/1880 | Van Eps | 417/472 |
| 2,686,006 | 8/1954 | Hasselquist | 417/472 X |
| 4,111,616 | 9/1978 | Rankin | 417/472 |
| 4,781,716 | 11/1988 | Richelsoph | 600/16 X |

FOREIGN PATENT DOCUMENTS

| | | |
|---|---|---|
| 2340755 | 2/1975 | Fed. Rep. of Germany . |
| 2567970 | 1/1986 | France .................. 417/472 |
| 7403309 | 5/1978 | Sweden . |

OTHER PUBLICATIONS

Rotellar, A Blood Pump Which Minimizes Haemolysis, Jan. 25, 1958, p. 197, The Lancel.
Derwant's abstract No. 858 816 E/26, SU H7554, 23 Jul. 1975.

Primary Examiner—Leonard E. Smith
Assistant Examiner—Eugene L. Szczecina, Jr.
Attorney, Agent, or Firm—Browdy and Neimark

[57] ABSTRACT

A blood pump, particularly intended as an extracorporeal blood pump, comprises a pump cylinder and two discs spaced apart in the longitudinal direction of the cylinder and substantially filling the cross-sectional area of the cylinder. The discs are reciprocatingly movable in accordance with a preferably variable movement pattern. Each of the discs is provided with a non-return valve means permitting fluid flow through the disc substantially solely in the desired direction of fluid transportation. The discs may be movable relative to the stationary pump cylinder surrounding the discs, or they may be firmly connected with the surrounding cylinder wall, which therewith accompanies the discs in their movements, the cylinder section between the discs having in this case a length which varies in response to the variation of the distance between the discs, and a correspondingly variable volume.

8 Claims, 1 Drawing Sheet 14,925,377

PUMP

Field of Invention

The present invention relates to a pump for pumping biological fluids, in particular blood.

The pump according to the invention has primarily been developed for use as an extracorporeal blood pump in conjunction, for instance, with surgical operations, dialysis, oxygenation processes, etc. It is also conceivable, however, for a pump according to the invention to be constructed in a manner which would enable it to be implanted in a patient, as an artificial heart.

BACKGROUND OF THE INVENTION

Extracorporeal blood pumps used today in conjunction with surgical procedures, dialysis, blood oxygenation, etc. are almost exclusively in the form of peristaltic roller pumps. Peristaltic pumps when used in the present context are encumbered with a number of serious drawbacks, however. For example, when pumping blood with the aid of a roller operated peristaltic pump it is difficult to prevent damage to blood corpuscles in the pumped blood, when the hose through which the blood is conducted is subjected to the pressure of the rollers. Thus, it is difficult to avoid part of the blood corpuscles present from being crushed and destroyed as the hose is compressed by the rollers acting thereon. Even though the compression rollers do not close the hose completely, but leave a narrow through passage, the flow velocities occuring in this narrow passage are so high as to cause damage to the blood corpuscles in the blood pumped therethrough. Another serious problem is encountered with the use of such pumps when the flow of blood to the inlet side of the pump radically diminishes or ceases completely, for example as a result of a blockage at the end of the catheter connecting the pump to a blood vessel. Such blockages are liable to occur with relative ease, for example as a result of abutment of the catheter orifice with the wall of the aforesaid blood vessel. In cases such as these a peristaltic pump will continue to carry out a pumping action, and in doing so will create on the inlet side of the pump subpressures of such magnitude as to cause serious injury to the patient connected to the pump. In addition it is difficult to adapt the flow and pressure characteristics of a peristaltic pump to what can be considered suitable characteristics from a physiological aspect. The use of especially designed centrifugal pumps as extracorporeal blood pumps has also been tried to some extent. Such pumps expose the pumped blood to extremely high shear forces, which are liable to damage the blood corpuscles. In order to achieve high pressures, it is necessary to employ extremely high rotational velocities.

SUMMARY OF THE INVENTION

Consequently, the object of the present invention is to provide an improved blood pump intended primarily for extracorporeal use, but which can also conceivably be constructed as an artificial heart for implantation.

BRIEF DESCRIPTION OF DRAWING

FIG. 1 is a cross-sectional view of a first embodiment of the invention.

FIG. 2 is a cross-sectional view of a second embodiment of the invention.

FIG. 3 is a cross-sectional view of a third embodiment of the invention.

DETAILED DESCRIPTION OF EMBODIMENTS

Figure 1:
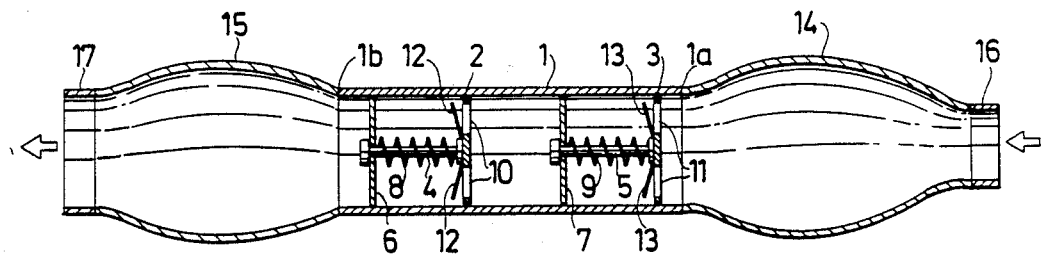
FIG. 1.

The pump according to the invention illustrated in FIG. 1 comprises a cylinder 1 which is made of some suitable material and has an inlet end 1a and an outlet end 1b. The cylinder 1 has a constant cross-section throughout its length. Spaced axially in the cylinder 1 are two discs or plates 2 and 3 which cover substantially the whole cross-sectional area of the cylinder. Each of the discs 2, 3 is carried by a respective spindle 4 and 5 each of which is journalled for axial movement in a respective stationary holder 6 and 7, the holders being so formed and being so arranged in the cylinder 1 as to enable the two discs to move reciprocatingly through a predetermined distance in the cylinder 1. The discs may be acted upon advantageously in one direction of movement thereof by respective springs 8 and 9, and driven in their opposite directions of movement by suitable drive means not shown. These drive means are located externally of the cylinder 1 and may be operated electromagnetically or by means of a permanent magnets. When the discs 2 and 3 incorporate parts comprising a magnetizable material or a permanently magnetic material, the externally located drive means may include electromagnets or movable permanent magnets, so that the two discs 2 and 3 can be driven backwards and forwards in the cylinder 1 by a magnetic driving co-action through the cylinder wall. It will be understood, however, that the discs can be driven in some other manner, e.g. mechanically or pneumatically, with the aid of appropriate drive means located externally of the cylinder 1. The disc drive means are preferably constructed so as to enable the two discs 2 and 3 to be driven individually of one another, so as to enable the mutual movement pattern of the discs to be changed as desired.

The discs 2 and 3 are each provided with a respective through-port 10 and 11, each having fitted therein a respective non-return valve, which in the illustrated embodiment has the form of a flap valve 12 and 13, which permit fluid to flow through the discs 2 and 3 in substantially only one direction, from the inlet end 1a of the cylinder 1 to the outlet end 1b thereof.

The diameter of the discs 2, 3 is preferably such that the peripheral edge or rim of respective discs terminates short of the inner wall surface of the cylinder 1, so as not to seal thereagainst and so as to leave sufficient clearance between the disc rim and said wall surface to ensure that blood corpuscles are not liable to be crushed upon reciprocating movement of the discs within the cylinder.

The inlet end 1a of the cylinder 1 is preferably connected to a fluid container of variable volume, for example a container in the form of a hose-connection 14 having a freely flexible hose wall. An advantage is afforded when the wall of the hose-connection 14 is "flacidly" flexible without being resilient, so that the internal volume of the hose-connection 14 is able to vary freely within certain limits, without the hose wall exerting appreciable pressure on the fluid enclosed. The outlet end 1b of the cylinder 1 is advantageously connected to a fluid container which has an elastically variable volume, e.g. a container in the form of a hose-connection 15 having an elastic hose wall which exerts a variable pressure on the fluid enclosed in the hose, in dependence on the extent to which the hose is stretched.

In the case of the illustrated exemplifying embodiment an inflexible ring 16 and 17 is fitted in a respective outer end of the hose-connections 14 and 15. The rings 16, 17 are stationarily mounted, as is also the cylinder 1, and can be connected to the fluid circuit in which the pump is to operate.

The hose-connection or container 14 functions as a volume equalizing or compensating vessel which compensates for pulsations in the flow of fluid pumped by the pump, so as to obtain a smooth and substantially more uniform flow of fluid through the circuit connected to the pump. Similarly, the hose-connection or container 15 also functions as a pressure equalizing or compensating vessel which takes up pulsative irregularities in the pressure generated by the pump, so that substantially solely minor pulsations occur in the circuit connected to the pump.

The fluid transporting properties of the pump can be varied within wide limits, by varying the movement pattern of the two discs 2, 3.

A maximum and substantially continuous flow of fluid through the pump, from its inlet to its outlet side, can be achieved, by driving the two discs 2, 3 simultaneously in mutually opposite directions, i.e. alternately towards and away from one another.

On the other hand, when the two discs 2, 3 are driven co-directionally in unison with one another, i.e. so that both discs always move in one and the same direction, the pump effect, i.e. the net flow through the pump, is substantially zero, though some movement of the blood to and fro is still generated in the circuit connected to the pump, which is an advantage from a physiological aspect. It shall be observed here that when the pump is connected to a closed circuit, such as to a blood circulatory system of a patient, the prevailing pressure on the outlet side of the pump is always higher than that on the inlet side thereof, and hence the valve flaps 12, 13 will remain closed when the two discs 2, 3 move simultaneously towards the inlet end.

Thus, both the magnitude of the flow through the pump and the flow pulsations, can be varied, by varying the mutual movement pattern of the two discs, between the aforesaid two extreme cases, i.e. the cases in which the discs either move in mutually opposite directions or in mutually the same direction. It shall be observed in this respect that the discs 2, 3 need not move at the same speed in both directions of movement. For example, the return stroke may be faster than the working stroke.

By suitable adaptation of the properties of the volume equalizing vessel 14 and the pressure equalizing vessel 15 and appropriate setting of the movement pattern of the two discs 2, 3, it is possible to transport through the pump a fluid flow of desired flow and pressure characteristics. Thus, a pump constructed in accordance with the invention can both receive and deliver a continuous and/or a pulsatile flow of fluid. Consequently, it is possible to achieve flow and pressure characteristics which are more favourable from a physiological aspect.

Another important advantage afforded by the pump according to the invention is that it is impossible for subpressures to be created on the inlet side of the pump.

The pump can be adjusted to a minimum operating pressure on the inlet side, by commensurate adjustment of the biassing force on the valve flaps 12, 13. This minimum operating pressure, however, can not be smaller than zero. With the pump tuned in this way, no fluid will be transported if the pressure on the pump inlet side tends to fall beneath the set value. Thus, should the flow of fluid to the inlet side of the pump decrease, the pump will automatically adjust to the flow available, therewith obviating any risk of injury to the patient connected to the pump. The pump is thus self-regulating and does not strive to pump larger quantities of fluid than those available.

Because a pump constructed in accordance with the invention is able to deliver continuously a substantially constant flow, it requires but little energy to operate the pump, particularly since it is not necessary to accelerate or decelerate the body of fluid pumped therethrough.

Figure 2:
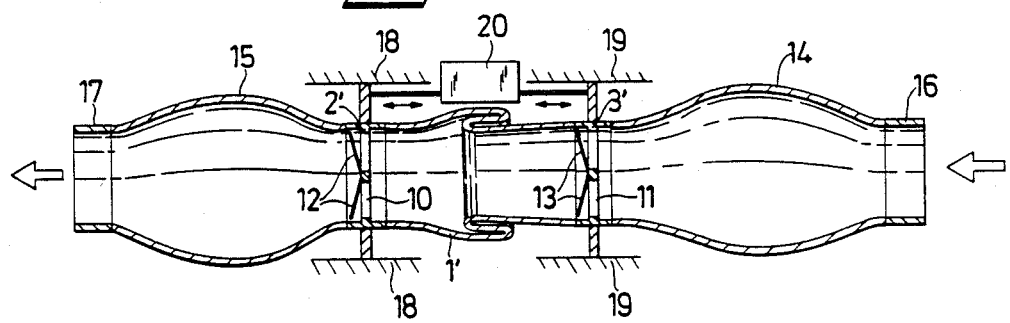
FIG. 2.

The embodiment of a pump according to the invention illustrated schematically in FIG. 2 differs from the aforedescribed embodiment illustrated in FIG. 1, primarily in that with the FIG. 2 embodiment the two pumping discs 2' and 3' are not axially movable within an encasing, stationary pump cylinder, but are instead firmly connected to the cylinder and can be said to constitute sections of the cylinder wall, these wall sections thus being reciprocatingly movable with the discs 2', 3'. For example, as illustrated schematically in FIG. 2, the discs 2', 3' may be guided for axial movement in respective outer stationary guide means 18 and 19, as schematically illustrated, and connected to suitable drive means 20 operative in driving the two discs 2', 3' backwards and forwards independently of one another, in accordance with a desired, preferably variably adjustable movement pattern. In this embodiment the intermediate part of the pump cylinder 1' that interconnects the two discs 2', 3' is constructed in a manner which enables the length of said cylinder part, and the volume presented thereby, to vary in dependence on the distance between the two movable discs 2', 3'. In the FIG. 2 embodiment this is achieved by giving the pump cylinder 1' a telescopic, bellows-like construction. It will be understood, however, that there are many ways in which the pump cylinder 1' connecting the discs 2', 3' can be constructed, in order to enable the axial length of the cylinder to vary in response to the pumping movements effected by the discs 2', 3', with a corresponding variation in effective cylinder volume. It will be understood that although the functional operating method of this embodiment of a pump according to the invention coincides fully with the method of operation of the pump described above with reference to FIG. 1, the FIG. 2 embodiment of the pump affords important practical advantages with regard to the driving of the two discs 2', 3', since the discs of this embodiment can be mechanically connected directly to the drive means 20 located externally of the pump cylinder.

A further important advantage afforded by the pump according to FIG. 2 is that the axial distance between the median positions of the two movable discs 2', 3' can be varied, i.e. the median length and therewith the median volume of the pump cylinder 1' connecting the two discs 2', 3'. This enables the volume of the circuit incorporating the pump to be varied, which is highly desirable when the pump is connected to a blood circulatory system of a patient. It is namely desirable in this latter case to be able to influence the pressure of the blood in the patient's circulatory system by varying the volume of the circuit. This can readily be achieved with the pump according to FIG. 2, without requiring a static auxiliary supply of blood, as in the case of the blood pumps used at present.

Figure 3:
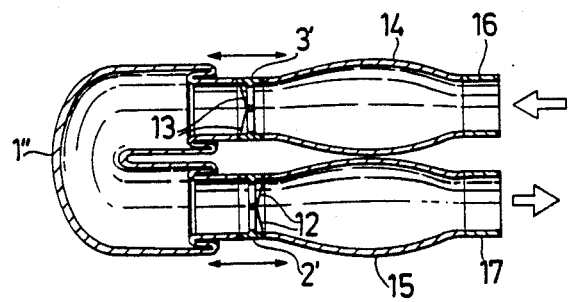
FIG. 3.

The pump illustrated schematically in FIG. 3 differs from the FIG. 2 pump embodiment in that the pump cylinder 1" interconnecting the two movable pump discs 2', 3' is, in this case, constructed in a manner which enables the cylinder to be bent substantially to a U-shaped configuration, such as to locate the discs 2', 3' in side-by-side relationship in their respective limbs of the U. The manner in which the two pump discs 2', 3' are journalled and driven has not been shown for the sake of simplicity, since the means used herefor may take many different forms and will be obvious to those of normal skill in the art who have read the above description of the FIG. 2 embodiment. The embodiment according to FIG. 3 operates in the same manner as the FIG. 2 embodiment and affords the same advantages thereas. An additional advantage afforded by the embodiment according to FIG. 3, however, is that the total external dimensions of the pump can be adapted to suit varying practical requirements, for example if the pump according to the invention is to be constructed as an artificial heart for implantation.

It will be understood from the aforegoing that also in the case of the FIG. 1 embodiment in which the pump discs 2, 3 are arranged for axial movement within and in relation to a surrounding, stationary pump cylinder, the part of the cylinder 1 located between the respective movement paths of the two discs may be constructed in accordance with FIG. 2 and FIG. 3, i.e. in a manner which enables the axial length of the interconnecting cylinder part to be varied, and therewith its volume, thereby to provide commensurate variation of the total volume of the pump circuit, or in a manner which enables the interconnecting cylinder part to be bent, e.g. to a U-form, in order to adjust the total external dimensions of the pump to suit prevailing circumstances.

If it is desired to assist the blood circulation in both the major and the minor circulatory systems of a patient, there can be used two pumps constructed in accordance with the invention, one for each circulatory system. These pumps can either be used individually, or may be combined to form a pump assembly driven by separate or common drive means. The two pumps can therewith readily be adapted to the flow and pressure desired in each of the two circulatory systems.

Such an assembly, comprising two pumps with associated drive means, can readily be given small dimensions and will consume so little energy as to enable it to be used as an artificial heart implant.

Although the pump according to the invention has been developed primarily for use as a blood pump, and has been described in the aforegoing chiefly with this use in mind, it will be understood that the pump can be used to pump other biological fluids which contain cells or organisms that are readily damaged when pumped by means of a peristaltic pump for example. It will be understood that a pump constructed in accordance with the invention as defined in the following claims may take many forms different to those illustrated and described here.

We claim:

1. A blood pump for connection to the blood circulatory system of a living being, comprising a pump chamber having an inlet opening at one end and an outlet opening at the opposite end, a first non-return valve located in said pump chamber adjacent its inlet opening for permitting a blood flow solely in the direction into said pump chamber through said inlet opening, a second non-return valve located in said pump chamber adjacent said outlet opening for permitting a blood flow solely in the direction out from said pump chamber through said outlet opening, said first and second non-return valves being mutually spaced as seen in the direction of extension of said pump chamber between said inlet opening and said outlet opening and each of said first and second non-return valves being individually reciprocatingly movable in said direction of extension and the volume of said pump chamber enclosed between said first and second non-return valves being variable and commensurate with the mutual spacing of said first and second non-return valves in said direction of extension, and individual controllable drive means for reciprocatingly moving said first and second non-return valve means, respectively, independently of one another in accordance with a controllable and variable pattern of mutual displacement, whereby blood can be pumped from said inlet opening to said outlet opening with a net flow variable in a controlled manner down to substantially zero without creation of a complete standstill of the blood in the pump and without creation of a sub-pressure at the inlet opening.

2. A blood pump as claimed in claim 1, wherein said pump chamber is stationary and said first and second non-return valves are movable within and in relation to the pump chamber.

3. A blood pump as claimed in claim 1, wherein said first and second non-return valves are firmly joined with the surrounding wall of said pump chamber, and the section of the pump chamber located between the two non-return valves has a variable length and a commensurate variable volume dependent on the mutual spacing of the two non-return valves.

4. A blood pump as claimed in claim 1, wherein the mean value of the volume of said pump chamber between said first and second non-return valves is variable in a controlled manner.

5. A blood pump as claimed in claim 1, wherein the extension of said pump chamber between said first and second non-return valves is substantially rectilinear.

6. A blood pump as claimed in claim 1, wherein the extension of said pump chamber between said first and second non-return valves is substantially U-shaped.

7. A blood pump as claimed in claim 1, comprising an inlet chamber connected to the inlet opening of said pump chamber, said inlet chamber having a variable volume and flaccid, substantially no pressure exerting walls, and an outlet chamber connected to the outlet opening of said pump chamber, said outlet chamber having a variable volume and resilient, pressure exerting walls.

8. A pump for biological fluids, particularly blood, comprising an elongate pump cylinder, two non-return valves located in said pump cylinder mutually spaced as seen in the longitudinal direction of the pump cylinder and each permitting a fluid flow solely in one direction through said pump cylinder, and drive means for displacing said non-return valves reciprocatingly relative to one another in the longitudinal direction of the pump cylinder for periodic variation of the volume in said pump cylinder enclosed between said two non-return valves, wherein the section of said pump cylinder located between said two non-return valves is flexible, such as to enable the geometric extension of said pump cylinder section to be varied between a substantially rectilinear extension to a substantially U-shaped extension.

* * * * *